United States Patent [19]

Chang et al.

[11] Patent Number: 4,562,175

[45] Date of Patent: Dec. 31, 1985

[54] SYNTHETIC PEPTIDES

[76] Inventors: Ding Chang, Peninsula Laboratories, Inc., 611 Taylor Way, Belmont, Calif. 94002; Akira Arimura; Michael D. Culler, both of Laboratories for Molecular Neuroendocrinology and Diabetes (LMNED) Bunker 15, Tulane University'S Herbert Research Center, Belle Chassee, La. 70037; Jaw-Kang Chang, Peninsula Laboratories, Inc., 611 Taylor Way, Belmont, Calif. 94002

[21] Appl. No.: 576,712

[22] Filed: Feb. 3, 1984

[51] Int. Cl.$^4$ .................... C07C 103/52; A61K 37/02
[52] U.S. Cl. ................................ 514/12; 260/112.5 R
[58] Field of Search ................. 260/112.5 R; 424/177

[56] References Cited

PUBLICATIONS

Spiess et al., *Nature*, vol. 303, Jun. 9, 1983, pp. 532–536.
Rivier et al., *Nature*, vol. 300, Nov. 18, 1982, pp. 276–278.
Spiess et al., *Biochemistry*, vol. 21, 1982, pp. 6037–6040.
Esch et al., *The J. Biological Chem.*, vol. 258, 1982, pp. 1806–1810.

Rivier et al., 8th *American Peptide Symposium*, May 22–27, 1983, Tucson, Ariz., p. 237.

*Primary Examiner*—Delbert R. Phillips
*Assistant Examiner*—F. T. Moezie
*Attorney, Agent, or Firm*—Cushman, Darby & Cushman

[57] ABSTRACT

A synthetic peptide growth hormone releasing factor having substantially the following amino acid sequence:

Thr—Ala—Asp—Ala—Ile—Phe—Thr—Asn—Ser—
1                              5

—Tyr—Arg—Lys—Val—Leu—Gly—Gln—Leu—Ser—
    10                              15

—Ala—Arg—Lys—Leu—Leu—Gln—Asp—Ile—Nle—
    20                              25

—Ser—Arg—Gln—Gln—Gly—Glu—Ser—Asn—Gln—
    30                              35

—Glu—Arg—Gly—Ala—Arg—Ala—Arg—Leu—NH$_2$
    40                              44 methods of inducing growth in an animal and growth inducing pharmaceutical compositions, including animal feed compositions, are disclosed.

4 Claims, No Drawings

SYNTHETIC PEPTIDES

BACKGROUND OF THE INVENTION

This application relates to the synthesis of novel synthetic peptides and in particular to the synthesis of growth hormone-releasing factors (GRF) and their non-naturally occuring analogs.

Growth hormone is one of the hormones secreted by the anterior pituitary. The presence of excess of growth hormone can cause giantism or acromegaly and insufficient secretion causes dwarfism. It effects the metabolism of protein as well as the metabolism of carbohydrates and lipids, and has been described as switching the source of fuel for the body from carbohydrate to fat. Human growth hormone has limited application as a treatment for puituitary dwarfism; see Goodman and Gilman, The Pharmacological Basis of therapeutics, 5th Edition, pp. 1376–1382 (1975).

Adenohypophysial function, including growth hormone (GH) secretion, is mediated by neurohumoral substances referred to as releasing and release inhibiting hormones or factors. Growth hormone secretion is stimulated by growth hormone-releasing factor (GRF). Peptides with GRF activity were isolated from human pancreatic tumor and the structure of this natural peptide was elucidated; Guillemin et al, Science 218: 582 (1982) and Rivier et al, Nature 300: 276 (1982). Considerable interest has developed in the identification and characterization of hypothalamic GRF and in their potential use as therapeutic and diagnostic agents. For instance, human pancreatic tumor GRF (hpGRF), having a known structure, undergoes a drastic loss of biological activity during storage or when introduced into a living system. This loss of activity is believed to be, at least partly, caused by the oxidation of methionine, an amino acid present in the 27th position of naturally occurring hpGRF.

DETAILED DESCRIPTION OF THE INVENTION

We have now found, and hereby disclose, a series of synthetic growth hormone-releasing factors resistant to oxidation and thereby possessing greater growth hormone-releasing activity than the naturally occurring compounds. The invention will be explained on the basis of hpGRF although it will be appreciated that the same principals apply to analogous growth hormone-releasing factors, as explained in detail below.

We have discovered and hereby disclose a potent stimulator of growth hormone release from the pituitary gland. The synthetic peptide is based upon the structure of the naturally occurring peptide isolated from a human pancreatic tumor and contains 44 amino acid residues. Our synthetic peptide substitutes norleucine at position 27 which is occupied by methionin in the natural compound. The amino acid sequence of norleucine[27]-human pancreatic growth hormone-releasing factor (Nle[27]-hpGRF) is as follows:

Thr—Ala—Asp—Ala—Ile—Phe—Thr—Asn—Ser—
1                   5

—Tyr—Arg—Lys—Val—Leu—Gly—Gln—Leu—Ser—
10                              15

—Ala—Arg—Lys—Leu—Leu—Gln—Asp—Ile—Nle—
20                              25

—Ser—Arg—Gln—Gln—Gly—Glu—Ser—Asn—Gln—
30                              35

—Glu—Arg—Gly—Ala—Arg—Ala—Arg—Leu—NH$_2$
40                              44

We have found that the amino acid methionin which occupies position 27 of the natural peptide is highly susceptible to oxidation, and that oxidation of methionine in this and other releated methionine-containing peptides results in a drastic loss of biological activity. Insertion of the structurally similar but stable norleucine at postion 27 produces a synthetic peptide resistant to oxidation which exhibits greater growth hormone-releasing activity than the natural compound.

Methionin is first oxidized to a sulfoxide derivative which can be reduced to the original form by a reducing agent. As oxidation contiues, however, methionin is converted into an irreversible sulfonic acid derivative. We have found that the addition of a reducing agent such as L-ascorbic acid to the test medium will enhance the GH-releasing activity of hpGRF as compared to the use of medium without a reducing agent. Addition of a reducing agent to the vehicle for hpGRF, however, will not fully protect hpGRF from oxidation due to the lability of the reducing agent itself. Loss of biologic activity through methionine oxidation is also observed with another releasing hormone, corticotropin-releasing factor. Thus, any means of preventing oxidation will enhance the biological activity of peptides in which reduced methionine is important for structural integrity and biological activity.

We reasoned that a structurally similar yet not readily oxidized amino acid such as norleucine could replace methionine in hpGRF, thus preventing oxidation without altering GH-releasing activity. It has been found that Nle[27]-hpGRF possesses greater GH-releasing activity than original hpGRF.

Other analogous growth hormone-releasing factors susceptible to a similar modification (exchange of norleucine for methionin in at least one position) within the ambit of our invention are:

[DAla[2], Nle[27]] hpGRF(1-44-NH$_2$)
[DAla[2], Nle[27]] hpGRF(1-29-NH$_2$)
[DAla[2], Nle[27]] Rat GRF(1-43-OH)
[DAla[2], Nle[27]] Rat GRF(1-29-OH)
[Dala[2], Nle[27]] hpGRF(1-28-NH$_2$)
[DAla[2], Nle[27]] Rat GRF(1-43-NH$_2$)
[DAla[2], Nle[27]] Rat GRF(1-29-NH$_2$)
[DAla[2], Nle[27]] Rat GRF(1-28-NH$_2$).

Norleucine and D-Alanine (DAla) are not naturally occurring amino acids and thus the peptides listed above are all synthetic substances.

The synthetic peptides according to the present invention are capable of a variety of physiological applications, in domestic animals as a growth stimulant for the increased production of meat, and in humans for the treatment of certain types of dwarfism due to growth hormone deficiency. The invention also comprehends formulations and mixtures containing the disclosed synthetic peptides, including animal feed supplements or additives, pharmaceutical and/or veterinary formulations, compositions and presentations.

There are various ways to synthesize the peptides of the present invention. The following is an outline of the Nle[27]-hpGRF synthesis.

Nle$^{27}$-hpGRF synthesis has been conducted by the solid method for peptide synthesis originally described by Merrifield (J. Am. Chem. Soc. 85: 2149, 1963). The synthesis commenced at the C-terminus of the peptide by coupling a protected α-amino acid to a suitable resin. Such starting material can be prepared by attaching the carboxyl group of tertial-butyloxy-carbonyl-leucine (BOC-leucine) to BHA resin. This step was followed by TFA deprotection, washing with methylene chloride, DMF, methylene chloride, and then neutralization with TFA, again washed with methylene chloride and DMF, then the next amino acid was coupled using dicyclohexyl-carbodiimide. Forthy-three cycles of a similar procedure were undertaken to complete 44 residue Nle$^{27}$-hpGRF. In case of coupling Asn and Gln, 1-hydroxylbenzotriazole (HOBT) was used to prevent dehydration of the side-chain of the amide group.

After washing the resin, it was dried in vacuum overnight, and then the peptide removed from the resin using HF in the presence of 10% anisole. The detached peptide was purified by gel filtration on Sephadex G-50, ion-exchange chromatography using carboxymethyl-cellulose-52 cation exchanger, partition chromatography on Sephadex G-50, and finally on the C-18 column.

The peptides of the present invention could be produced by a skilled investigator with proper equipment and who knows the amino acid sequence of hpGRF. Access to the cell line from which the natural material was isolated is not necessary to produce the synthetic material.

EXAMPLE

The synthesis of [Nle$^{27}$] hpGRF(1-44-NH$_2$) having the formula Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-Gln-Gln-Gly-Gln-Ser-Asn-Gln-Glu-Arg-Gly-Ala-Arg-Ala-Arg-Leu-NH$_2$.

The synthesis was conducted in a stepwise manner on a p-methylbenzhydrylamine hydrochloride resin (Omega Organics, Inc.) with 0.35 meg/g substitution. Three grams of this resin were neutralized with a 10% (by volume) solution of Et$_3$N in Ch$_2$Cl$_2$ for 10 min. The resin was recovered by filtration, washed with additional CH$_2$Cl$_2$, and stirred overnight with 2.5 equivalents of Boc-Leu and dicyclohexycarbodiimide in CH$_2$Cl$_2$. The following procedure was used to couple each new amino acid to the growing peptide chain:

The resin was washed three times with CH$_2$Cl$_2$, twice with EtOH, three times with CH$_2$Cl$_2$, then prewashed once with 40% (by volume) trifluoroacetic acid in CH$_2$Cl$_2$. The BOC group was removed by treatment with 40% trifluoroacetic acid in CH$_2$Cl$_2$ for 30 min. The resin was washed three times with CH$_2$Cl$_2$, twice with EtOH, three times with CH$_2$Cl$_2$, the prewashed twice with 10% Et$_3$N in CH$_2$Cl$_2$. The amino group was liberated with the trifluoroacetic acid salt by treatment with 10% Et$_3$OH in CH$_2$Cl$_2$, twice with EtOH, then three times with CH$_2$Cl$_2$. Except for incorporation of Asn$^{8,35}$, Gln$^{16,24,30,31,36}$, the coupling was performed in the following way: a 3-fold excess (3 mM) of the appropriate Boc-amino acid, dissolved in 25 ml of CH$_2$Cl$_2$ was added to the resin. After stirring for 2 min, a 3-fold excess of dicyclohexylcarbodiimide (DCC) (3 mM) in 10 ml of CH$_2$Cl$_2$ was added. The mixture was allowed to react for 2 hr. Asn$^{8,35}$ and Gln$^{16,24,30,31,36}$ were incorporated by the DCC and hydroxybenzotriazole (HOBT) method, using 3-fold excess of HOBT and 3-fold excess DCC in DMF and CH$_2$Cl$_2$ mixture. In all cases, the resin was washed three times with CH$_2$Cl$_2$, twice with EtOH and three times with CH$_2$Cl$_2$. Forty-three successive cycles of deprotection, neutralization, and coupling were carried out in this manner with the following amino acid derivatives: Boc-Arg (TOS), Boc-Ala, Boc-Arg (TOS), Boc-Ala, Boc-Gly, Boc-Arg (TOS), Boc-Glu (OBzl), Boc-Gln/HOBT, Boc-Asn/HOBT, Boc-Ser (OBzl), Boc-Glu (OBzl), Boc-Gly, Boc-Gln/HOBT, Boc-Gln/HOBT, Boc-Arg (TOS), Boc-Ser (OBzl), Boc-Met, Boc-Ile, Boc-Asp (OBzl), Boc-Gln/HOBT, Boc-Leu, Boc-Lys (Cl-z), Boc-Arg (TOS), Boc-Ala, Boc-Ser (OBzl), Boc-Leu, Boc-Gln/HOBT, Boc-Gly, Boc-Leu, Boc-Bal, Boc-Lys (Cl-Z), Boc-Arg (TOS), Boc-Tyr (Br-z), Boc-Ser (OBzl), Boc-Asn/HOBT, Boc-Ths (OBzl), Boc-Phe, Boc-Ile, Boc-Ala, Boc-Asp (OBzl), Boc-Ala and Boc-Tyr(Br-z).

The completeness of coupling was monitored by the ninhydrin color test procedure of Kaiser et al (Anal. Biochem. 34, 595–598, 1970). At the conclusion of the synthesis the protected peptide resin was washed with CH$_2$Cl$_2$, then treated with 40% TFA for 30 min., washed with CH$_2$Cl$_2$EtOH, and CH$_2$Cl$_2$ and dried under reduced pressure. The weight was 6.1 g. Cleavage of the protecting groups, and formation of the carboxyl terminal amide were effected with 60 ml of distilled HF in the presence of 7.5 ml anisole for 30 min. at −20° C. and 30 min. at 0° C. After removal of the excess HF under reduced pressure, the resin was washed with EtOAc to remove anisole, followed by 10% aqueous AcOH to extract the peptide. The crude lyophilized product (1.52 g) was subjected to gel filtration chromatography on a 5×49 cm column of Sephadex G-50, eluted with 30% HOAC with detection of the peptide peaks by UV at 278 nm and gave 557 mg of partially purified (Nle$^{27}$) hpGRF (1-44-NH$_2$). This partially purified (Nle$^{27}$) hpGRF(1-44-NH$_2$) was applied to a carboxymethyl cellulose-52 cation exchange column (2.5×15 cm), eluted with an NH$_4$OAc gradient from 0.01 M NH$_4$OAc (pH 4.5) to 0.3 M HN$_4$OAc (pH 6.5) and gave 285 mg of partially purified (Nle$^{27}$) hpGRF (1-44-NH$_4$). This 285 mg was subjected to partition chromatography on a 4.5×20 cm column of Sephadex G-50, eluted with the system BuOH:pyr:EtOH:0.2N-HOAc (4:1:1:7) to give 167 mg, which was reapplied twice using the same system to yield 29.9 mg of pure peptide.

In vitro analysis of the synthetic peptide: The synthetic Nle$^{27}$-hpGRF was added to the medium of monolayer rat pituitary cell cultures and incubated. After incubation, the media was assayed for GH released from the pituitary cells and compared to control cultures (medium alone). The amount of GH released in response to varying doses of Nle$^{27}$-hpGRF was compared to the GH release induced by the same concentrations of the synthetic hpGRF. The hpGRF and Nle$^{27}$-hpGRF were tested at the same time under identical conditions with the result that Nle$^{27}$-hpGRF possesses significantly greater biological activity than synthetic hpGRF.

What is claimed is:

1. A synthetic peptide growth hormone releasing factor having the following amino acid sequence:

Thr—Ala—Asp—Ala—Ile—Phe—Thr—Asn—Ser—
1                               5

-continued

—Tyr—Arg—Lys—Val—Leu—Gly—Gln—Leu—Ser—
10                              15

—Ala—Arg—Lys—Leu—Leu—Gln—Asp—Ile—Nle—
20                              25

—Ser—Arg—Gln—Gln—Gly—Glu—Ser—Asn—Gln—
30                              35

-continued
—Glu—Arg—Gly—Ala—Arg—Ala—Arg—Leu—NH$_2$.
40                              44

2. A method of inducing growth in an animal comprising administering to said animal a growth-inducing amount of the synthetic peptide of claim 1.

3. A growth inducing pharmaceutical composition comprising an effective, growth-inducing amount of the synthetic peptide of claim 1 together with a pharmaceutically acceptable carrier or diluent.

4. An animal feed composition comprising a growth-inducing amount of the synthetic peptide of claim 1 together with at least one compatible animal nutrient.

* * * * *